US00PP14761P2

(12) United States Plant Patent
Fear et al.

(10) Patent No.: US PP14,761 P2
(45) Date of Patent: May 4, 2004

(54) RASPBERRY PLANT NAMED 'DRISCOLL CARMELINA'

(50) Latin Name: *Rubus idaeus*
Varietal Denomination: Driscoll Carmelina

(75) Inventors: Carlos D. Fear, Aptos, CA (US); Richard E. Harrison, Aptos, CA (US); Fred M. Cook, Aptos, CA (US); Gavin Sills, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 10/306,456

(22) Filed: Nov. 27, 2002

(51) Int. Cl.[7] ..... A01H 5/00
(52) U.S. Cl. ..... Plt./204
(58) Field of Search ..... Plt./204

*Primary Examiner*—Anne Marie Grunberg
*Assistant Examiner*—Susan B. McCormick-Ewoldt
(74) *Attorney, Agent, or Firm*—Pennie & Edmonds LLP

(57) ABSTRACT

The present invention relates to a new and distinct cultivar of raspberry plant named Driscoll Carmelina. The new cultivar is distinguished from other raspberry cultivars by its late primocane production, high spring yields, good flavor and disease resistance. The new cultivar is distinguished from its seed parent by having better release from the receptacle, firmer fruit and better spring bud break. The new cultivar is distinguished from its pollen parent by producing firmer fruit with better shipping characteristics.

3 Drawing Sheets

Latin name of the genus and species of the plant claimed: The variety is botanically identified as *Rubus idaeus* L.

1. BACKGROUND OF THE INVENTION

The new cultivar of raspberry plant was developed from the hybridization of the selection 'P362.1' (an unpatented variety) as the seed parent with the selection 'N119.1' (an unpatented variety) as the pollen parent. The parents were crossed in 1995, whereafter fruit and seed were collected to produce seedlings for field planting in Watsonville, Calif. in 1995. The new cultivar was selected from these seedlings in 1997 for its large size, good flavor, and productivity. The new cultivar has been asexually propagated by in vitro shoot tip culture, root sucker division and root cuttings at the Cassin Ranch in Santa Cruz county, Calif. and has been shown to maintain the desired and distinguishing characteristics after propagation over several generations.

Latin name of the genus and species of the plant claimed: The variety is botanically identified as *Rubus idaeus* L.

2. SUMMARY OF THE INVENTION

The present invention provides a new and distinct cultivar of red raspberry plant named 'Driscoll Carmelina'. The cultivar is botanically identified as *Rubus idaeus* L. The 'Driscoll Carmelina' red raspberry plant produces a primocane crop which begins in late July and continues until early November. The floricane crop begins in late May and continues until mid-July. Floricane yields are high relative to other comparable varieties. The fruit of 'Driscoll Carmelina' has consistently good flavor and the fruit separates easily from its receptacle.

3. BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

4. DETAILED BOTANICAL DESCRIPTION

Figure 1:
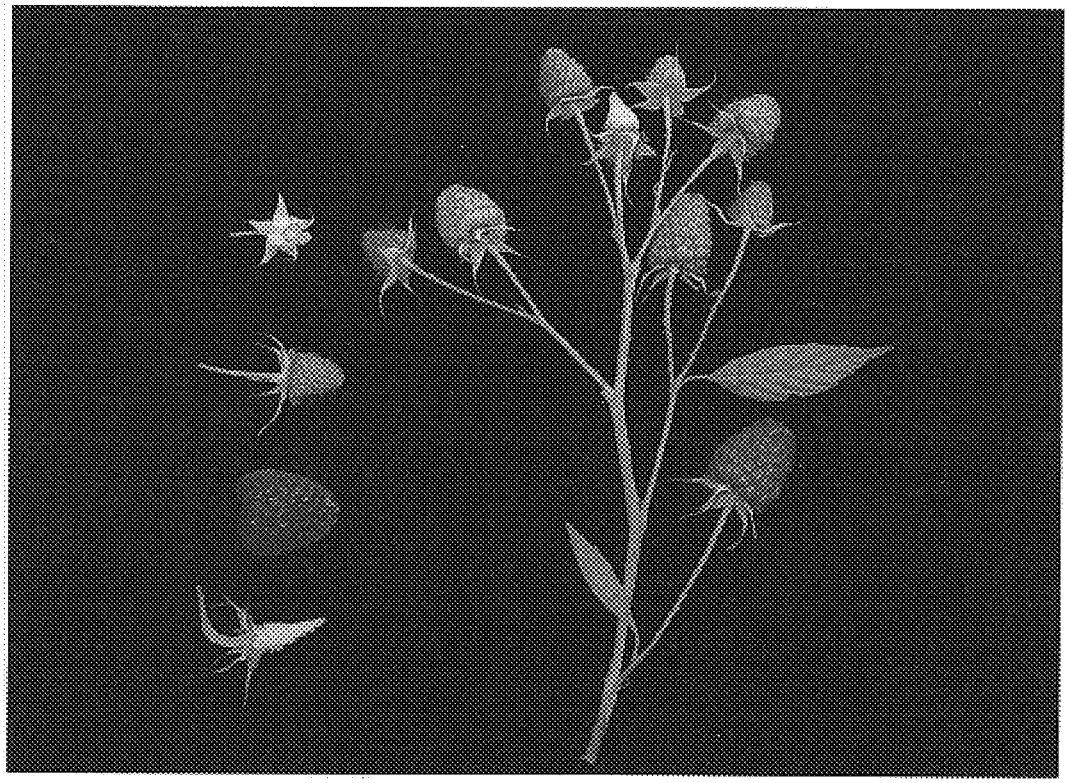
FIG. 1 is a photograph of a 'Driscoll Carmelina' primocane flowers and fruit in various stages of development.
Figure 2:
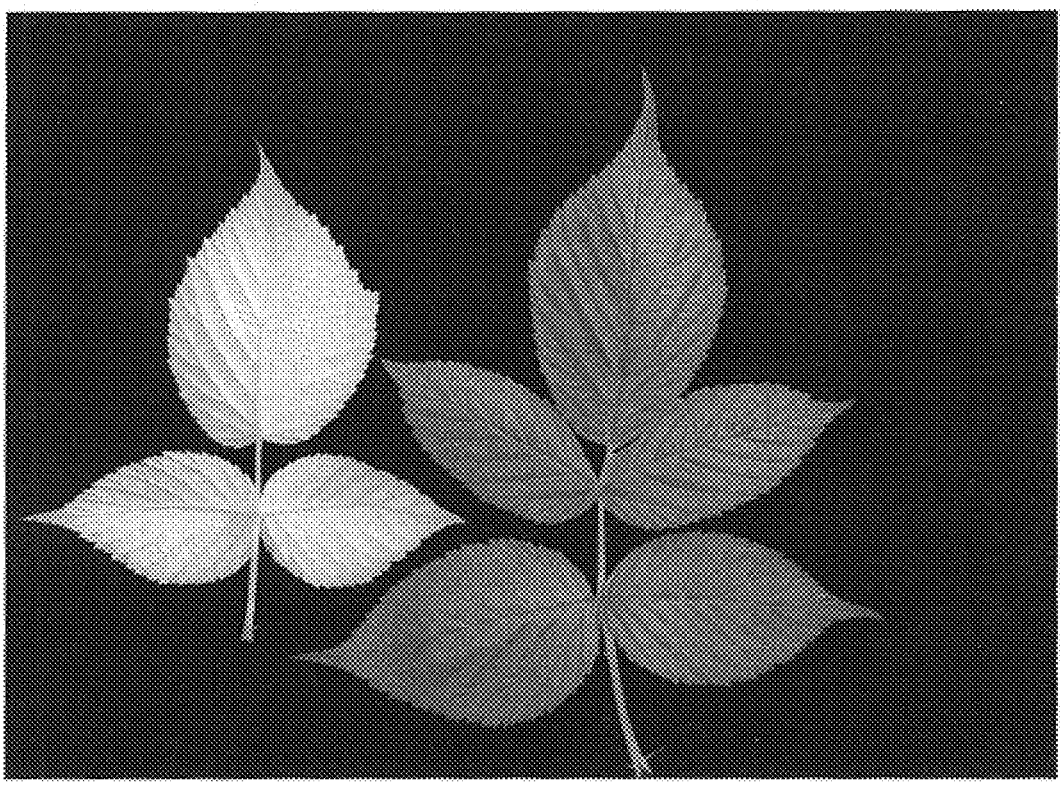
FIG. 2 is a photograph of a 'Driscoll Carmelina' primocane leaves showing upper and lower surfaces.
Figure 3:
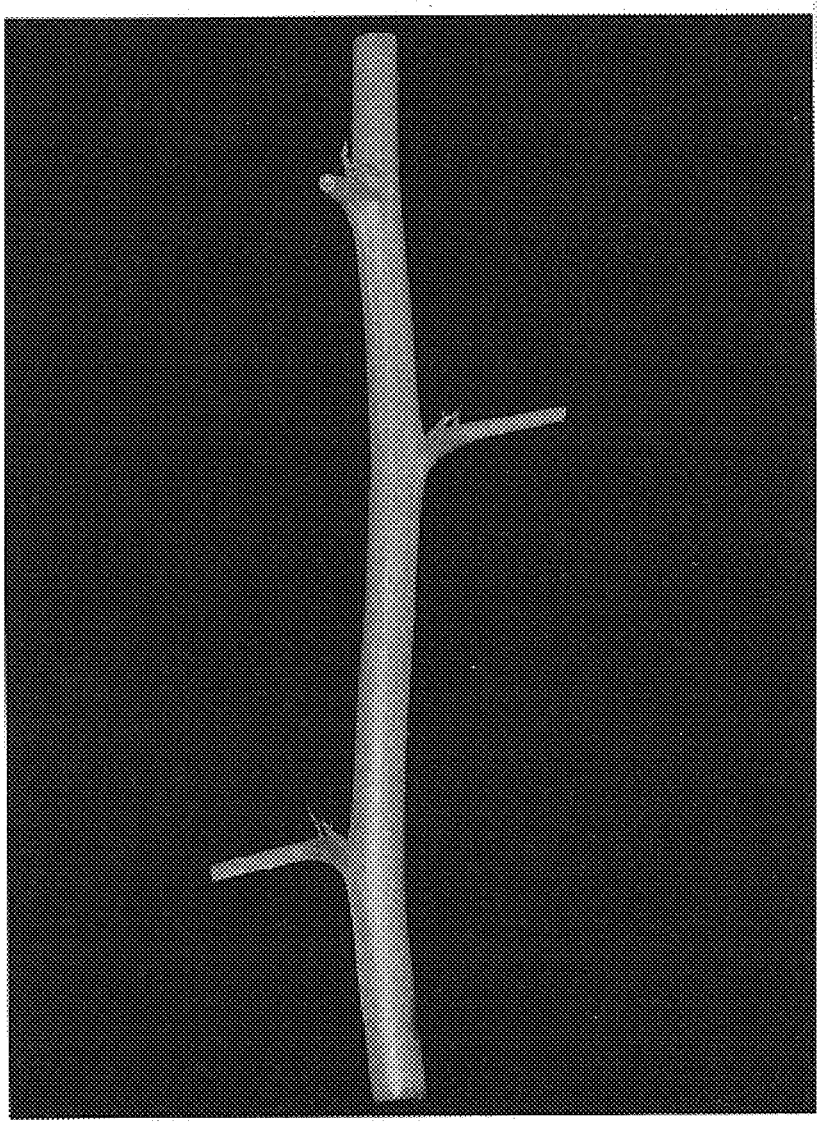
FIG. 3 is a photograph of a 'Driscoll Carmelina' primocane shoot.

The following detailed description of the new raspberry cultivar, 'Driscoll Carmelina', is based upon observations taken of 7 to 17 month old plants and fruit grown in Watsonville, Calif. between 2001 and 2002, and is believed to apply to plants of the 'Driscoll Carmelina' cultivar grown in similar conditions of soil and climate elsewhere.

Throughout this specification, color names beginning with a small letter signify that the name of the color, as used in common speech, is aptly descriptive. Color data followed by an alphnumeric code indicates the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new cultivar 'Driscoll Carmelina' compared with characteristics of the unpatented raspberry cultivar 'Heritage'. Observations of the cultivars were taken under similar conditions.

The new variety is particularly characterized and distinguished from other cultivars by its late primocane production, high spring yields, good flavor and disease resistance.

The fruit color of 'Driscoll Carmelina' is a deep red at harvest. Fruit of 'Driscoll Carmelina' separates easily from the receptacle and is of good firmness at harvest. The fruit of 'Driscoll Carmelina' is very consistent in size and shape throughout the harvest period. There were an average of 17 young shoots in the observed plants of 'Driscoll Carmelina' and the shoots emerged around February 22nd. The pigmentation color of both surfaces of the petals is 155D and there are five petals per flower. The color of the seeds of 'Driscoll Carmelina' is 161A, the average seed weight is about 1.4 mg, and there are an average of about 91 seeds per fruit.

The floricane yields of 'Driscoll Carmelina' are high relative to the variety 'Heritage'.

'Driscoll Carmelina' is distinguishable from its pollen parent, selection 'N119.1', by producing firmer fruit with better shipping characteristics. The new cultivar is distinguished from its seed parent, selection 'P362.1', by having better release from the receptacle, firmer fruit and better spring bud break.

4.1. DISEASE AND STRESS RESISTANCE

The cultivar has good tolerance to late leaf rust. Resistance to root rots is intermediate to other varieties. Cold tolerance of the new cultivar has not been established. Post harvest fruit rot resistance is good in comparison over many selections and varieties.

TABLE 1

PLANT CHARACTERISTICS OF 'DRISCOLL CARMELINA'

| | Driscoll Carmelina | Heritage |
|---|---|---|
| General | | |
| Plant size | | Large |
| Growth habit | Semi-erect | Erect |
| Productivity | High | Medium |
| Self-fruitfulness | Self-fruitful | Self-fruitful |
| Time of bud burst | Medium | Late |
| Primocane fruiting | | |
| Percent of cane length flowering as primocane | 10–30 | 20–40 |
| Percent of total yield | 37 | 53 |
| Primocanes | | |
| Number of young shoots | Medium | Medium |
| Young shoot pigmentation | Weak | Medium |
| Length (cm) | 249 | 196 |
| Time of shoot emergence | Early | Very late |
| Glaucosity (waxy bloom) | Strong | Weak |
| Strength | Medium | Medium |
| Cane Cross section from mid cane of primocane) | Rounded to angular | Rounded |
| Dormant cane color | brown to purple brown | brown to purple brown |
| Prickles | | |
| Pigmentation | green | green-brownish to green |
| Density on young shoots | Sparse | Dense |
| Attitude of tip | Downward | Downward |
| Size: Length (base to tip at 1 m height at end of harvest) (mm) | 1.2 | 2.3 |
| Texture | smooth | Rigid |
| Presence and distribution on petioles | Present irregularly | Present irregularly distribtuted |
| Pubescence on canes | Absent | Absent |
| Internodal distance (cm) (at central ⅓ of cane) | 5.0 | 5.3 |

TABLE 1-continued

PLANT CHARACTERISTICS OF 'DRISCOLL CARMELINA'

| | Driscoll Carmelina | Heritage |
|---|---|---|
| LEAVES | | |
| Color | | |
| Face | 147A | 147A |
| Relief between veins | Weak | Very weak |
| Glossiness | Medium | Medium |
| Underside | 148C | 148B |
| Petiole length (cm) | 6.1 | 7.7 |
| Stipule orientation | Erect | Erect |
| Arrangement | Compound | Compound |
| Number of leaflets | Sometimes 3, sometimes 5 | Sometimes 3, sometimes 5 |
| Overlapping of lateral leaflets | Free to touching | Free to touching |
| Lateral leaflet: length of stalket (lower pair) | Very short | Very short |
| Terminal leaflet | | |
| Length (cm) | 12.4 | 14.6 |
| Width (cm) | 8 | 7.8 |
| Shape | Ovate | Ovate |
| Tip | Acuminate | Acuminate |
| Base | Cordate | Acute to rounded |
| Margin | Doubly serrate | Doubly serrate |
| Lateral leaflets (basal pair) | | |
| Length (cm) | 10 | 14.7 |
| Width (cm) | 5.6 | 8.6 |
| Overlap | Yes | Free |
| Orientation | Opposite | Opposite |
| Shape | Ovate | Ovate |
| Tip | Acuminate | Acuminate |
| Base | Round | Oblique |
| Margin | Doubly serrate | Doubly serrate |
| Rachis length between terminal leaflet and adjacent lateral leaflets (cm) | 3.5 | 1.5 |
| FLOWERS | | |
| Flowering period | | |
| Primocane | 19 weeks, Late May–late September | 19 weeks, Late May–late September |
| Floricane | 10 weeks, Early April–late June | 10 weeks, Late March–mid June |
| Flower diameter (cm) | 1.5 | 1.8 |
| Petal | | |
| Length (cm) | 0.7 | 0.8 |
| Width (cm) | 0.4 | 0.3 |
| Pedicel coloration | | Present, strong intensity |
| FRUIT | | |
| Harvest season | | |
| Primocane | Mid July–early Nov | Early July–early November |
| Floricane | Late May–late July | Late May–late July |
| Fruting lateral | | |
| Length (4th lateral from tip) (cm) | 82.0 | 49.8 |
| Number of fruit per lateral | 22.1 | 20.3 |
| Color | | |
| Immature | 47A | 42C |
| Maturing | 185A | 46A |
| Mature fruit | 46A | 59A |
| Glossiness | Weak | Medium |
| Shape | Elliptic | Ovate |

TABLE 1-continued

| PLANT CHARACTERISTICS OF 'DRISCOLL CARMELINA' | | |
|---|---|---|
| | Driscoll Carmelina | Heritage |
| Dimensions | | |
| Size | Medium | Small |
| Length (mm) | 22.3 | 17 |
| Width (mm) | 20 | 18 |
| Length:width | 1.05 | 0.94 |
| Weight (g/fruit) | | |
| Primocane | 4.1 | 3.1 |
| Floricane | 3.8 | 2.3 |
| Soluble solids (%) | 10.4 | 10.8 |
| Titratable acidity (% as citric acid) | 1.57 | 1.58 |
| Seed Weight (mg) | 2.6 | 1.5 |
| Number druplets/fruit | 91 | 72 |
| Adherence to plug | Medium | Medium |
| Firmness | Medium | Firm |
| Yield | High | Medium |

4.2. NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531-5). Using a variety of oligonucleotide primers, alone or in combination, RAPD analysis of Driscoll Carmelina and Heritage yielded DNA fragment patterns that uniquely distinguish each of thses genetically distinct genotypes.

We claim:

1. A new and distinctive cultivar of raspberry plant, substantially as shown and described.

* * * * *